United States Patent [19]

Yagihara et al.

[11] 4,228,233
[45] Oct. 14, 1980

[54] PHOTOGRAPHIC SILVER HALIDE LIGHT-SENSITIVE MATERIAL

[75] Inventors: Morio Yagihara; Yukio Yokota, both of Minami-ashigara, Japan

[73] Assignee: Fuji Photo Film Co., Ltd., Minami-ashigara, Japan

[21] Appl. No.: 944,834

[22] Filed: Sep. 22, 1978

[30] Foreign Application Priority Data

Sep. 22, 1977 [JP] Japan .................. 52/114268

[51] Int. Cl.³ .............................. G03C 7/00
[52] U.S. Cl. ................... 430/385; 430/553; 430/558
[58] Field of Search .................. 96/100, 55, 56.6; 430/385, 553, 558

[56] References Cited

U.S. PATENT DOCUMENTS

| | | | |
|---|---|---|---|
| 3,171,740 | 3/1965 | Menzel et al. | 96/100 |
| 3,644,498 | 2/1972 | Loria | 96/100 |
| 3,737,316 | 6/1973 | Salminen et al. | 96/56.6 |
| 3,930,866 | 1/1976 | Oishi et al. | 96/100 |
| 3,933,501 | 7/1976 | Cameron et al. | 96/74 |
| 4,012,258 | 3/1977 | Kojima et al. | 96/100 |
| 4,126,462 | 11/1978 | Endo et al. | 96/56.6 |

*Primary Examiner*—Travis Brown
*Attorney, Agent, or Firm*—Sughrue, Rothwell, Mion, Zinn and Macpeak

[57] ABSTRACT

A photographic silver halide light-sensitive emulsion containing a cyan dye forming, colorless coupler having, at the coupling position, an alkoxy group having at least one sulfonamido or sulfamoyl group as a substituent and represented by one of the following general formulae (I) and (II):

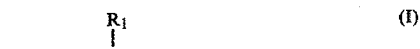

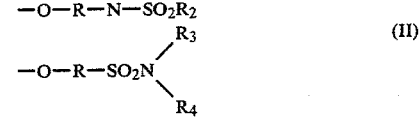

wherein R represents a saturated or unsaturated, divalent aliphatic group (except those having an aryl group as a substituent on the carbon atom adjacent the oxygen atom bonded to the coupling position); $R_1$, $R_3$ and $R_4$, which may be the same or different, each represents a hydrogen atom, an aliphatic group, or an aromatic group; and $R_2$ represents an aliphatic group, an aromatic group or a heterocyclic group; and wherein $R_3$ and $R_4$ can combine to form a ring; a photographic silver halide light-sensitive element comprising a support having thereon at least one silver halide emulsion layer and containing at least one of the cyan dye-forming, colorless couplers described above; and an image formation method using the same.

9 Claims, No Drawings

PHOTOGRAPHIC SILVER HALIDE LIGHT-SENSITIVE MATERIAL

BACKGROUND OF THE INVENTION

1. Field of the Invention

This invention relates to a new type of photographic color coupler, photographic color materials containing the same, and, further, to a method of image formation using such photographic color couplers.

2. Description of the Prior Art

As is well known in the art, dye images can be formed by imagewise exposure of a silver halide photographic material followed by color development whereby the oxidation product of an aromatic primary amine developing agent reacts with a dye forming coupler.

Generally speaking, this dye image method is based on the subtractive color reproduction principle, with cyan, magenta and yellow dye images, each of which is in a complementary relationship to red, green and blue light, respectively, being produced. For example, cyan dye images are generally produced from couplers comprising phenol or naphthol derivatives. The reaction between the coupler and the color developing agent takes place at the active sites of the coupler. One mole of a so-called "four-equivalent coupler" in which all of the active sites are substituted with hydrogen atoms theoretically requires on a stoichiometric basis 4 moles of silver halide as developing nuclei. On the other hand, two-equivalent couplers are known which have substituents releasable as anions at the active sites and which require only 2 moles of silver halide as developing nuclei. Accordingly, by use of 2-equivalent couplers, the amount of silver halide in the photographic coating can be generally reduced and, hence, the coating thickness thereof can be reduced. This, in turn, enables the processing time to be decreased and simultaneously results in the sharpness of the resulting dye images being advantageously improved. A variety of such coupling releasable groups are known including, for example, the sulfonamido groups set forth in U.S. Pat. No. 3,737,316, the imide groups set forth in U.S. Pat. No. 3,749,735, the sulfonyl groups set forth in U.S. Pat. No. 3,622,328, the allyloxy groups set forth in U.S. Pat. No. 3,476,563, the acyloxy groups set forth in U.S. Pat. No. 3,311,476, the thiocyano groups set forth in U.S. Pat. No. 3,214,437, the isothiocyanate groups set forth in U.S. Pat. No. 4,032,345, the sulfonyloxy groups set forth in U.S. Pat. No. 4,046,573, the thiocarbonyloxy groups set forth in Japanese patent Application (OPI) No. 51939/1977 (The term "OPI" as used herein refers to a "published unexamined Japanese patent application"), the aralkenylcarbonyloxy groups set forth in Japanese Patent Application (OPI) Nos. 39126/1978 and 39745/1978, the S-substituted monothiocarbonyloxy groups set forth in Japanese Patent Application (OPI) No. 45524/1978, the propionyloxy groups set forth in Japanese Patent Application (OPI) No. 47827/1978, the

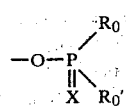

groups set forth in U.S. Pat. No. 4,072,525, and the substitued alkoxy groups set forth in U.S. Pat. Nos. 3,227,551 and 4,052,212 and Japanese Patent Application (OPI) Nos. 120334/1975, 18315/1977, 90932/1977 and 52423/1978.

Further, if the coupler contains a suitable type of coupling releasable group, for example, one which forms a diffusible dye structure, such a coupler, referred to as a diffusible dye releasing coupler, such can be employed in a diffusion transfer process in which the released dye is used to provide a dye image in an image receiving layer. Diffusible dye releasing couplers are described in, for example, U.S. Pat. Nos. 3,227,550, 3,765,886, U.S. Defensive Publication T900,029, British Pat. No. 1,330,524, etc. Besides, certain 2-equivalent, colored couplers exhibit a masking effect to correct undesirable absorptions of dyes as described in, for example, Japanese Patent Application (OPI) No. 26034/1976.

Furthermore, 2-equivalent couplers, which are referred to as development inhibitor releasing couplers, are known. Since these couplers release compound suppresses or inhibits development, these couplers are quite effective in improving image graininess, gradation control as well as improving color reproduction characteristics. These couplers can also be used in a diffusion transfer process because they affect a layer adjacent the layer in which they are present. Examples of these couplers are described in U.S. Pat. No. 3,227,554, Japanese Patent Application (OPI) No. 122335/1974 and German Patent Application (OLS) No. 2,414,006.

Since a 2-equivalent coupler has a wider range of applications as compared with a 4-equivalent coupler, the photographic industry tends to use this type of coupler more frequently.

However, most prior art 2-equivalent cyan dye forming couplers have certain disadvantages including insufficient coupling reactivity, the tendency to form color stains, poor dispersion stability which causes difficulties during coating, lack of storage stability, insufficient fastness of the resulting dye image in the finished product, etc.

SUMMARY OF THE INVENTION

Accordingly, one object of the present invention is to provide a new class of 2-equivalent cyan dye forming couplers free of the above-described disadvantages.

Another object of the present invention is to provide a method of forming cyan dye image through development of an imagewise exposed silver halide photographic emulsion in the presence of a new class of 2-equivalent coupler.

Still another object of the present invention is to provide a silver halide color photographic material containing a new class of couplers and to provide a method of photographic processing based on this class of couplers.

It has now been found, after extensive investigations, that the above cited and other objects of this invention are achieved by colorless cyan dye forming couplers having at the coupling position, as a coupling off groups, at least one alkoxy group substituted with at least one of a sulfonamido group or a sulfamoyl group represented by the following general formulae (I) or (II):

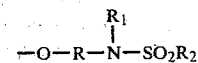

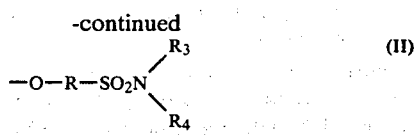

wherein R represents a saturated or unsaturated divalent aliphatic group (except those having an aryl group as a substituent on the carbon atom adjacent the oxygen atom bonded to the coupling position); $R_1$, $R_3$ and $R_4$, which may be the same or different, each represents a hydrogen atom, an aliphatic group, or an aromatic group; and $R_2$ represents an aliphatic group, an aromatic group or a heterocyclic group; and wherein $R_3$ and $R_4$ can combine to form a ring.

Accordingly, in one embodiment of this invention, this invention provides a photographic silver halide light-sensitive emulsion containing at least one of the cyan dye-forming colorless photographic couplers as described above.

In a further embodiment of this invention, this invention provides a photographic silver halide light-sensitive element comprising a support having thereon at least one silver halide emulsion layer containing at least one of the cyan dye-forming, colorless photographic couplers as described above.

In a still furhter embodiment of this invention, this invention provides a method for forming an image comprising imagewise exposing a photographic silver halide light-sensitive material comprising a support having thereon at least one silver halide emulsion layer, and developing the exposed silver halide photographic material with a color developer containing an aromatic primary amine developing agent in the presence of at least one cyan dye-forming, colorless photographic coupler as described above.

DETAILED DESCRIPTION OF THE INVENTION

The groups represented by general formulae (I) and (II) above are split off when cyan dyes are formed by the coupling reaction with the oxidized product of a primary amine developing agent. In the general formulae (I) and (II), R represents a saturated or unsaturated divalent aliphatic group which may contain 1 to 4 carbon atoms, and which may be straight or branched chain, for example, methylene, dimethylene, trimethylene, 1-methyldimethylene, tetramethylene and propenylene. R may also be substituted with one or more substituents other than a sulfonamido or sulfamoyl group. Examples of suitable additional substituents on R include a halogen atom (for example, fluorine, chlorine and bromine), an aryl group (for example, phenyl), etc. (However, divalent aliphatic groups in which an aryl group is substituted on the carbon atom adjacent the oxygen atom bonded to the coupling position are not suitable.)

$R_1$, $R_3$ and $R_4$, which may be the same or different, each represents a hydrogen atom, an aliphatic group or an aromatic group, and $R_2$ represents an aliphatic group, an aromatic group or a heterocyclic group. Further, $R_3$ and $R_4$ can combine and form a ring.

More specifically, $R_1$ represents a hydrogen atom; a straight chain, branched chain or cyclic aliphatic group containing 1 to 7 carbon atoms (i.e., an alkyl group, an alkenyl group and an aralkyl group each containing up to 7 carbon atoms) (e.g., methyl, ethyl, propyl, isopropyl, etc.); or a mono- or bi-cyclic aromatic group containing 6 to 12 carbon atoms (e.g., phenyl tolyl, etc.).

$R_2$ represents a straight chain, branched chain or cyclic aliphatic group containing 1 to 18 carbon atoms (i.e., an alkyl group, an alkenyl group and an aralkyl group each containing up to 18 carbon atoms) (e.g., methyl, ethyl, propyl, octyl, hexadecyl, benzyl, etc.); a mono- or bi-cyclic aromatic group containing 6 to 12 carbon atoms (e.g., phenyl, tolyl, naphthyl, etc.); or a 5- or 6-membered heterocyclic group which may be condensed with a benzene ring and which can include one or more of a nitrogen atom, an oxygen atom or a sulfur atom as hetero atoms (e.g., thiazolyl, benzothiazolyl, oxazolyl, pyridyl, 1,2,4-triazolyl, pyrazolyl, benzimidazolyl, imidazolyl, etc.).

$R_3$ and $R_4$, which may be the same or different, each represents a hydrogen atom; a straight chain, branched chain or cyclic aliphatic group containing 1 to 18 carbon atoms (i.e., an alkyl group, an alkenyl group, and an aralkyl group each containing up to 18 carbon atoms) (e.g., methyl, ethyl, propyl, isopropyl, cyclopropyl, octyl, hexadecyl, etc.); or a mono- or bi-cyclic aromatic group containing 6 to 12 carbon atoms (e.g., phenyl, naphthyl, tolyl, etc.).

The term "colorless" couplers as used herein means those couplers whose molecular extinction coefficient at the absorption maximum thereof does not exceed 5,000 within the visible spectrum.

Since the colorless 2-equivalent cyan dye forming coupler of the present invention exhibits a higher rate of dye formation than prior art couplers containing an alkoxy group mainly due to the coupling-off group characteristic of the invention, a photographic material using the colorless cyan dye forming coupler has a high photographic speed, an improved gradation and a maximum density when processed using not only conventional processing but also using a rapid processing, in particular. The coupler of the present invention shows a low tendency to fog and color stain formation, and, moreover, has excellent dispersibility in various coatings used in multilayer photographic materials at higher content levels. Further, the cyan dyes resulting from this type of cyan coupler have a superior fastness to light, heat and humidity, free from undesired spectral absorption.

Preferred couplers of the present invention have the general formulae (Ia) and (IIa):

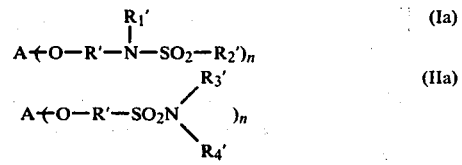

In the formulae (Ia) and (IIa), A represents an n-valent cyan coupler residue (e.g., a naphthol or phenol nucleus), and R' represents a saturated or unsaturated divalent straight chain or branched chain aliphatic group containing 1 to 4 carbon atoms (e.g., alkylene such as methylene, dimethylene, trimethylene, 1-methyldimethylene, tetramethylene, propenylene, etc.), which may be substituted. Suitable substituents for R' are one or more of those substituents as described above for R in the general formulae (I) and (II).

$R'_1$ represents a hydrogen atom, an alkyl group containing 1 to 7 carbon atoms which may be straight chain, branched chain or cyclic (e.g., methyl, ethyl, propyl, isopropyl, etc.), an alkenyl group containing 2 to 7 carbon atoms which may be straight chain, branched chain or cyclic (e.g., allyl, etc.), an aralkyl group containing 7 carbon atoms (e.g., benzyl) or an aryl group containing 6 to 12 carbon atoms which may be mono- or bi-cyclic (e.g., phenyl, tolyl).

$R'_2$ represents an alkyl group containing 1 to 18 carbon atoms which may be straight chain, branched chain or cyclic (e.g., methyl, ethyl, propyl, octyl, octadecyl, etc.), an alkenyl group containing 2 to 18 carbon atoms which may be straight chain, branched chain or cyclic (e.g., vinyl, etc.), an aralkyl group containing 7 to 18 carbon atoms in which the alkyl moiety may be straight chain, branched chain or cyclic and in which the aryl moiety may be mono- or bi-cyclic (e.g., benzyl, etc.), an aryl group containing 6 to 12 carbon atoms which may be mono- or bi-cyclic (e.g., phenyl, tolyl, etc.) or a heterocyclic group (e.g., thiazolyl, benzothiazolyl, oxazolyl, benzimidazolyl, pyridyl, etc.).

$R'_3$ and $R'_4$, which may be the same or different, each represents a hydrogen atom, an alkyl group containing 1 to 18 carbon atoms which may be straight chain, branched chain or cyclic (e.g., methyl, ethyl, propyl, isopropyl, octyl, octadecyl, etc.), an alkenyl group containing 2 to 18 carbon atoms which may be straight chain, branched chain or cyclic (e.g., allyl, etc.), an aralkyl group containing 7 to 18 carbon atoms in which the alkyl moiety may be straight chain, branched chain or cyclic and in which the aryl moiety may be mono- or bi-cyclic (e.g., benzyl, etc.) or an aryl group containing 6 to 12 carbon atoms which may be mono- or bi-cyclic (e.g., phenyl, tolyl, etc.).

The alkyl groups, the alkenyl groups and the aryl groups represented by $R'_1$, $R'_2$, $R'_3$ or $R'_4$ and the heterocyclic groups represented by $R'_2$ may be substituted with one or more of a halogen atom (e.g., F, Cl or Br), a nitro group, a cyano group, a hydroxyl group, a carboxyl group or a sulfo group, etc.

Further, $R'_3$ and $R'_4$ may combine and form a ring. Suitable rings formed by $R'_3$ and $R'_4$ include, for example, piperidine, piperadine, pyrrolidine, pyrrole, morpholine, imidazole, benzimidazole, 1,2,4-triazole, 1,2,3-triazole, benzotriazole, etc., rings.

The most preferred positions for substitution of the sulfonamido group or the sulfamoyl group on the alkoxy group in the general formulae (Ia) and (IIa) are the $\alpha$-, $\beta$- and $\gamma$-positions to the alkoxy group.

n represents a positive integer of 1, 2 or more.

The cyan coupler residue in the structure shown by the general formula (Ia) or (IIa) above is the part remaining after removal of the hydrogen atoms or coupling-off groups from the active sites of the cyan coupler. Where plural active sites are present in the same coupler molecule, the coupling-off groups, including hydrogen atoms, substituted at these active sites may be the same or different. Most preferably, however, all active positions of the coupler should be substituted with coupling-off groups represented by the general formula (I) or (II) in accordance with the present invention.

Although the most preferred value for n is 1 or 2, n can have a value of 3 or more if, for example, the cyan coupler comprises a polymerized coupler.

Of the couplers of the present invention, the most useful couplers are represented by either of the following general formulae (III) and (IV).

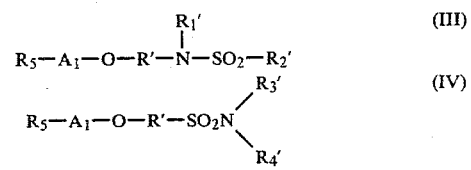

In the general formulae (III) and (IV), $A_1$ represents a cyan dye-forming coupler residue containing a phenol nucleus or an $\alpha$-naphthol nucleus.

The group represented by the formula

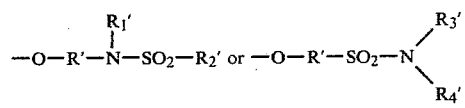

which is substituted at the coupling site of the coupler residue is released when oxidative coupling takes place with an aromatic primary amine developing agent to produce a cyan dye.

$R'$, $R'_1$, $R'_2$, $R'_3$ and $R'_4$ each has the same meaning as described with respect to the general formulae (Ia) and (IIa).

$R_5$ represents a hydrogen atom, an aliphatic group containing up to 30 carbon atoms which may be straight chain, branched chain or cyclic (e.g., methyl, isopropyl, pentadecyl, eicosyl and like alkyl groups), an alkoxy group containing up to 30 carbon atoms in which the alkyl moiety may be straight chain, branched chain or cyclic (e.g., methoxy, isopropoxy, pentadecyloxy, eicosyloxy, etc.), an aryloxy group which may be mono- or bi-cyclic (e.g., phenoxy, p-tert-butylphenoxy, etc.), an acylamido group, a sulfonamido group, a phosphoramido group or a ureido group, each represented by one of the following general formulae (V) to (VIII).

or a carbamyl group represented by the general formulae (IX) or (X).

B and B' in the general formulae (V) to (X) above, which may be the same or different, each represents an aliphatic group containing 1 to 32 carbon atoms (preferably a straight chain or branched chain alkyl group containing 1 to 20 carbon atoms, such as methyl, ethyl, propyl, isopropyl, butyl, octyl, dodecyl, hexadecyl, etc.), a cycloalkyl group (e.g., containing 3 to 12 carbon atoms, such as cyclopropyl, cyclohexyl, norbornyl, etc.) or an aryl group which may be mono- or bi-cyclic (e.g., phenyl, naphthyl, etc.). The alkyl and the aryl group may be substituted with one or more of a halogen atom (e.g., F, Cl, etc.), a nitro group, a cyano group, a hydroxyl group, a carboxy group, an amino group (e.g., an amino group, an alkylamino group, a dialkylamino group, an anilino group, an N-alkylanilino group, etc.), an alkyl group (such as those described above), an aryl group (e.g., phenyl, acetylaminophenyl, etc.), an alkoxycarbonyl group (e.g., tetradecyloxycarbonyl, etc.), an acyloxycarbonyl group, an amido group (e.g., acetamido, methanesulfonamido, etc.), an imido group (e.g., succinimido, etc.), a carbamoyl group (e.g., N,N-dihexylcarbamoyl, etc.), a sulfamoyl group (e.g., N,N-diethylsulfamoyl, etc.), an alkoxy group (e.g., ethoxy, tetradecyloxy, octadecyloxy, etc.), an aryloxy group (e.g., phenoxy, p-tert-butylphenoxy, 2,4-diamylphenoxy, 4-hydroxy-3-tert-butylphenoxy, etc.) and C and C', which may be the same or different, each represents the groups described above for B and additionally an —OB group, an —NH—B group, and an —NB$_2$ group.

Of the compounds represented by the general formulae (III) and (IV) described above, particularly preferred compounds are described below.

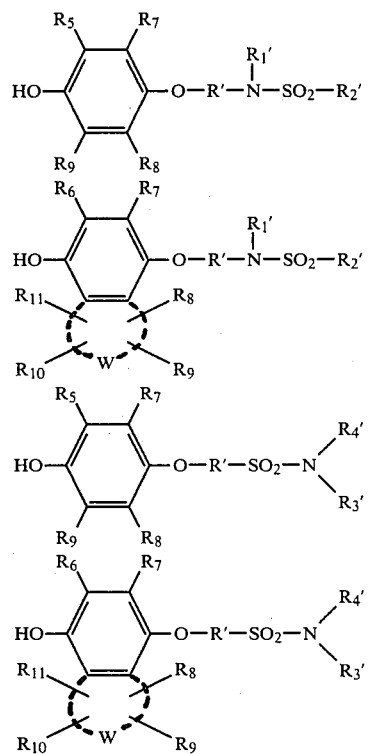

R', R'$_1$, R'$_2$, R'$_3$, R'$_4$ and R$_5$ in the general formulae (XI) to (XIV) have the same meaning as described in the general formulae (III) and (IV). R$_6$ is a hydrogen atom, an aliphatic group containing up to 30 carbon atoms, more preferably from 1 to 20 carbon atoms (e.g., methyl, isopropyl, hexadecyl, etc.) or a carbamoyl group represented by the formula (IX) and (X) described above defining R$_5$ in the general formulae (III) and (IV). R$_7$, R$_8$, R$_9$, R$_{10}$ and R$_{11}$, which may be the same or different, each represents a hydrogen atom, a halogen atom, an alkyl group, an aryl group, an alkoxy group, an alkylthio group, a heterocyclic ring, an amino group, a carbonamido group, a sulfonamido group, a sulfamyl group or a carbamyl group. More specifically, R$_7$ represents a hydrogen atom, a halogen atom (e.g., Cl, Br, etc.), a primary, secondary or tertiary straight chain, branched chain or cyclic alkyl group containing 1 to 22 carbon atoms (e.g., methyl, propyl, isopropyl, n-butyl, sec-butyl, tert-butyl, hexyl, dodecyl, 2-chlorobutyl, 2-hydroxyethyl, 2-phenylethyl, 2-(2,4,6-trichlorophenyl)ethyl, 2-aminoethyl, etc.), an alkylthio group containing 1 to 20 carbon atoms wherein the alkyl moiety can be straight chain, branched chain or cyclic (e.g., hexydecylthio, etc.), an aryl group containing 6 to 20 carbon atoms wherein the aryl moiety can be mono- or bi-cyclic (e.g., phenyl, 4-methylphenyl, 2,4,6-trichlorophenyl, 3,5-dibromophenyl, 4-trifluoromethylphenyl, 2-trifluoromethylphenyl, 3-trifluoromethylphenyl, naphthyl, 2-chloronaphthyl, 3-ethylnaphthyl, etc.), a heterocyclic group (e.g., benzofuranyl, furanyl, thiazolyl, benzothiazolyl, naphthothiazolyl, oxazolyl, benzoxazolyl, naphthoxazolyl, pyridyl, quinolinyl, etc.), an amino group (e.g., amino, an alkylamino group containing 1 to 20 carbon atoms wherein the alkyl moiety can be straight chain, branched chain or cyclic, such as methylamino, diethylamino, dodecylamino, etc., an arylamino group containing 6 to 20 carbon atoms wherein the aryl moiety can be mono- or bicyclic, such as phenylamino, tolylamino, 4-(3-sulfobenzamido), anilino, 4-cyanophenylamino, 2-trifluoromethylphenylamino, etc., a heterocyclic amino group, such as benzothiazolamino, etc.), a carbonamido group (e.g., an alkylcarbonamido group containing 1 to 20 carbon atoms wherein the alkyl moiety can be straight chain, branched chain or cyclic, such as ethylcarbonamido, decylcarbonamido, phenylethylcarbonamido, etc.; an arylcarbonamido group containing 6 to 20 carbon atoms wherein the aryl moiety can be mono- or bi-cyclic, such as phenylcarbonamido, 2,4,6-trichlorophenylcarbonamido, 4-methylphenylcarbonamido, 2-ethoxyphenylcarbonamido, 3-[α-(2,4-di-tert-amylphenoxy)acetamido]benzamido, naphthylcarbonamido, etc.; a heterocyclic carbonamido group, such as thiazolylcarbonamido, benzothiazolylcarbonamido, naphthothiazolylcarbonamido, oxazolylcarbonamido, benzoxazolylcarbonamido, imidazolylcarbonamido, benzimidazolylcarbonamido, etc.), a sulfonamido group (e.g., an alkylsulfonamido group containing 1 to 20 carbon atoms wherein the alkyl moiety can be straight chain, branched chain or cyclic, such as butylsulfonamido, dodecylsulfonamido, phenylethylsulfonamido, etc.; an arylsulfonamido group containing 6 to 20 carbon atoms wherein the aryl moiety can be mono- or bicyclic, such as phenylsulfonamido, 2,4,6-trichlorophenylsulfonamido, 2-methoxyphenylsulfonamido, 3-carboxyphenylsulfonamido, naphthylsulfonamido, etc.; a heterocyclic sulfonamido group, such as thiazolylsulfonamido, benzothiazolylsulfonamido, imidazolylsulfonamido, benzimidazolylsulfonamido, pyridylsulfonamido, etc.), a sulfamyl group (e.g., an alkylsulfamyl group containing 1 to 20 carbon atoms wherein the alkyl moiety can be straight chain, branched chain or cyclic, such as propylsulfamyl, octylsulfamyl, pentadecylsulfamyl, octadecylsulfamyl, etc.; an arylsulfamyl group containing 6 to 20 carbon atoms wherein the aryl moiety can be mono- or bi-cyclic, such as phenylsulfamyl, 2,4,6-trichlorophenylsulfamyl, 2- methoxyphenylsulfamyl, naphthylsulfamyl, etc.; a heterocyclic sulfamyl group, such as thiazolylsulfamyl, benzothiazolylsulfamyl, oxazolylsulfamyl, benzimidazolylsulfamyl, pyridylsulfamyl, etc.) and a carbamyl group (e.g., an alkylcarbamyl group containing 1 to 20 carbon atoms wherein the alkyl moiety can be straight chain, branched chain or cyclic, such as ethylcarbamyl, octylcarbamyl, pentadecylcarbamyl, octadecylcarbamyl, etc.; an arylcarbamyl group containing 6 to 20 carbon atoms wherein the aryl moiety can be mono- or bicyclic, such as phenylcarbamyl, 2,4,6-trichlorophenylcarbamyl, etc., and a heterocyclic carbamyl group, such as thiazolylcarbamyl, benzothiazolylcarbamyl, oxazolylcarbamyl, imidazolylcarbamyl, benzimidazolylcarbamyl, etc.). Specific examples for $R_8$, $R_9$, $R_{10}$ and $R_{11}$ include those described above for $R_7$, while W represents the non-metallic atomic group necessary to complete a 5- or 6-membered ring, both carbocyclic or heterocyclic containing one or more of an oxygen atom, a sulfur atom and a nitrogen atom as hetero atoms, such as benzene, cyclohexene, cyclopentene, thiazole, oxazole, imidazole, pyridine, pyrrole, etc. The most preferred ring formed by W is a benzene ring.

Representative examples of the coupler of the present invention are set forth below, but the present invention is not to be construed as being limited to these examples.

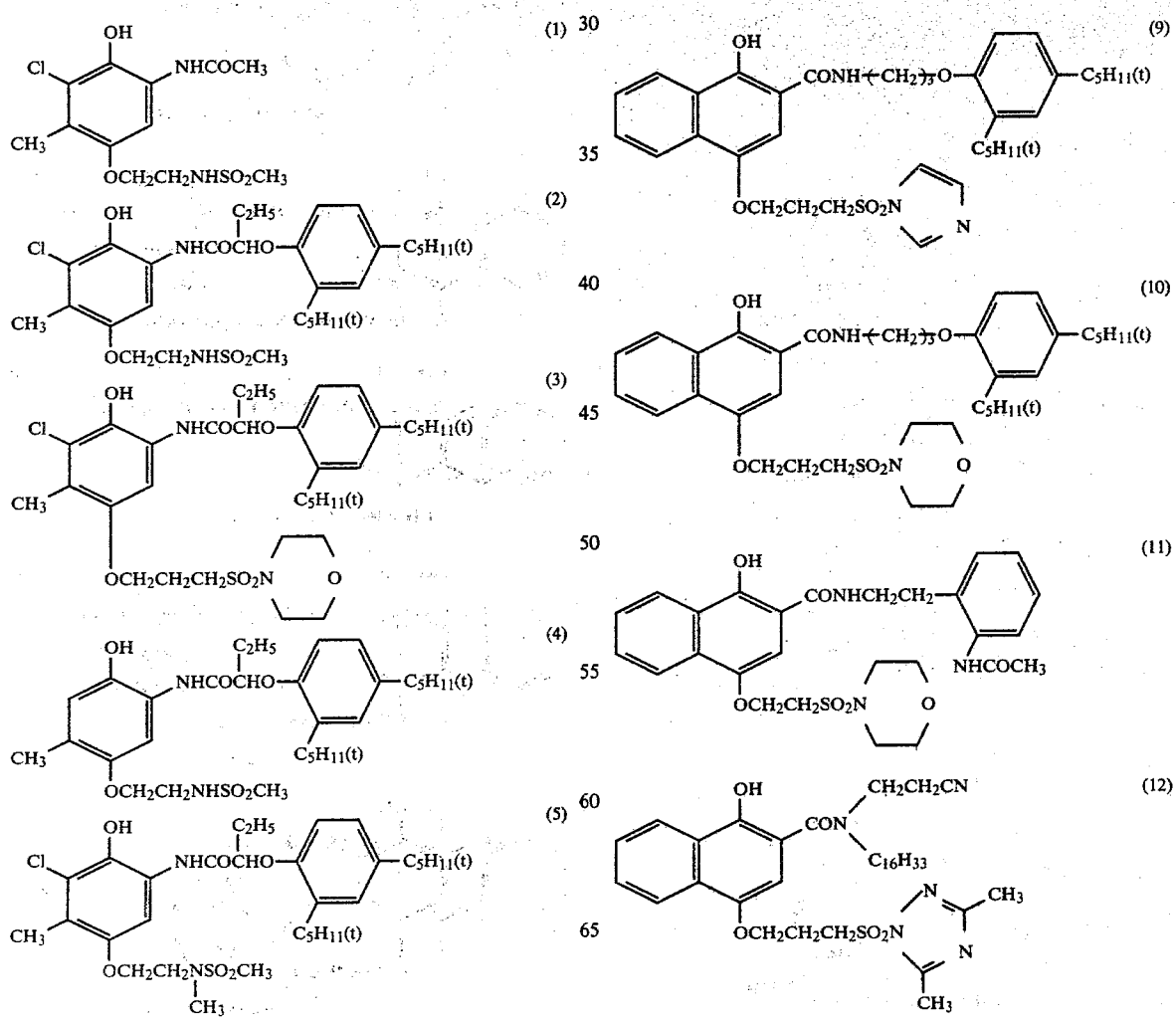

-continued
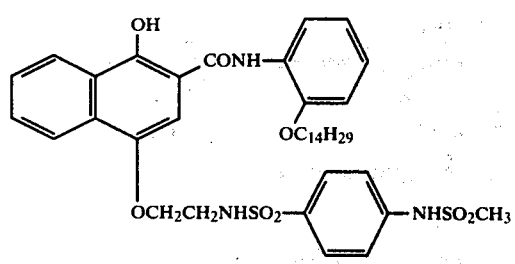 (13)
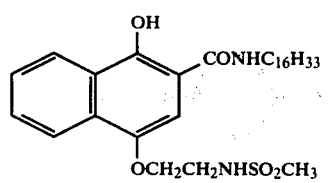 (14)
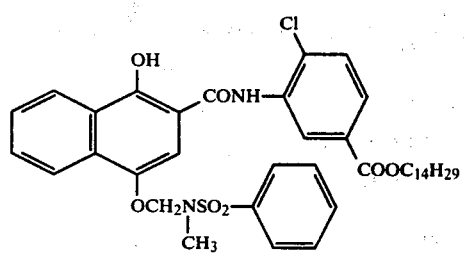 (15)
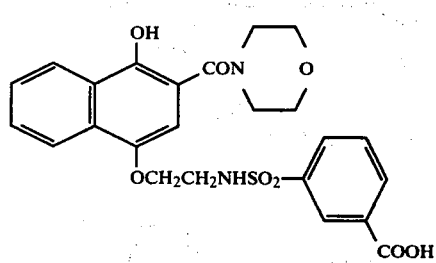 (16)
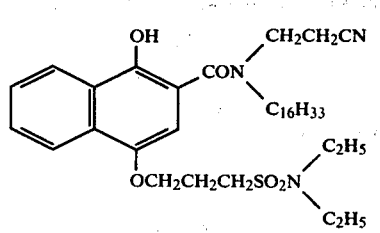 (17)
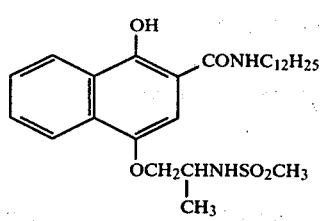 (18)
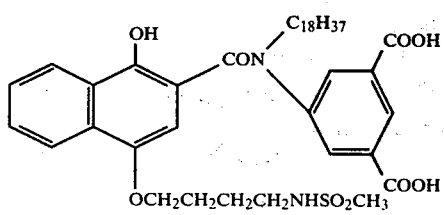 (19)
-continued
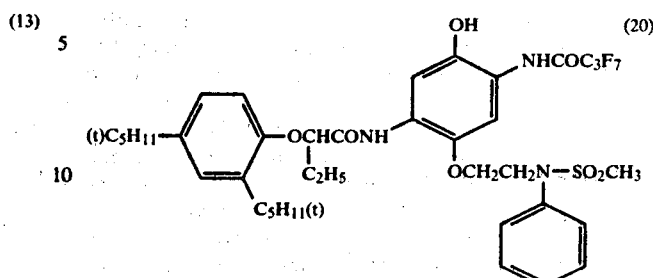 (20)
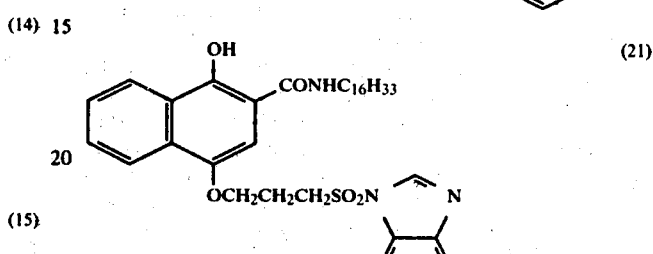 (21)
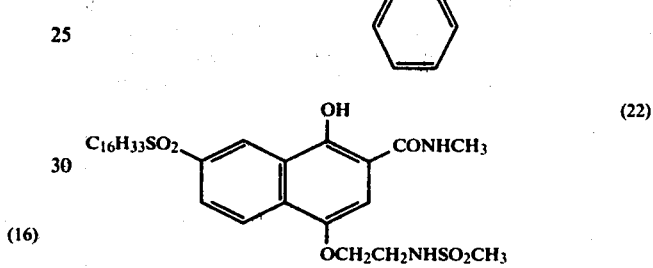 (22)
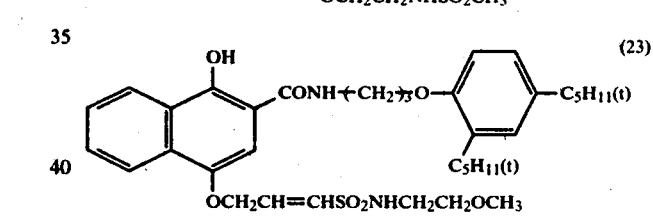 (23)
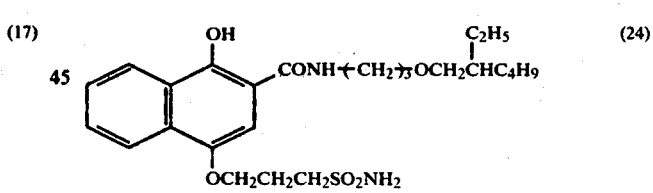 (24)
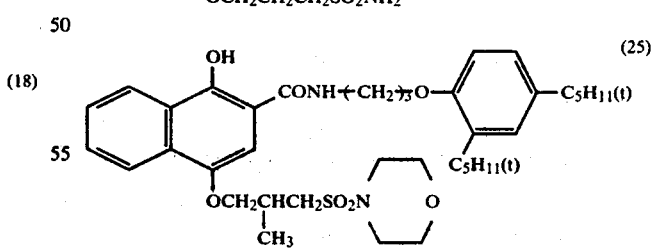 (25)
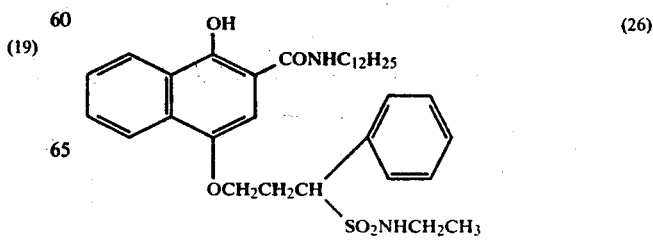 (26)

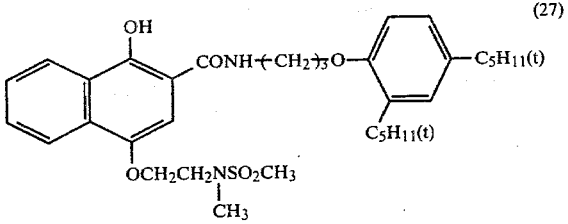

These and other compounds of the present invention can be synthesized using the following procedures.

1,4-Dihydroxy-2-naphthoic acid can be reacted with a substituted alkyl halide in a solvent, such as acetone, dimethylformamide (DMF), etc., in the presence of an alkaline compound, such as pyridine, sodium carbonate, sodium hydroxide, a sodium alkoxide, etc., at room temperature (about 15° to about 30° C.) or elevated temperature (about 30° to about 60° C.). 1,4-Dihydroxy-2-naphthoic acid can be prepared (1) by Kolbe Reaction of 1,4-dihydroxynaphthalene as disclosed in Russig. F., *J. Prakt Chem* (2) 62, 33 (1900) or (2) by the method disclosed in J.A.C.S., 64, 798, (1942). Suitable substituted alkyl halides are those including a sulfonamido group or a sulfamoyl group as a substituent. Alkyl halides substituted with a sulfonamido group can be prepared (1) in general, by reacting an amino alcohol (e.g., ethanolamine, 3-amino-propanol, N-methylaminoethanol, N-phenylaminoethanol) with sulfuryl chloride to obtain a sulfonamido alcohol derivative and, then, chlorinating the sulfonamido alcohol derivative with a chlorinating agent (e.g., thionyl chloride) or (2) by reacting a chloroalkylamine hydrochloride with sulfuryl chloride as described in Japanese Patent Publication No. 20492/1976. Alkyl halides substituted with a sulfamoyl group can be prepared, in general, by chlorinating a sulfoalcohol with a chlorinating agent (e.g., thionyl chloride, phosphorus pentachloride, etc.) to obtain a chlorosulfonylalkyl chloride and, then, reacting the chlorosulfonylalkyl chloride with an amine. For example, the preparation of γ-chloropropylsulfonyl chloride is described in Kogyo Kagaku Zasshi, page 1028, Vol. 59, No. 9 (1956) and Japanese Patent Publication No. 172/1971. A suitable molar ratio of the 1,4-dihydroxy-2-naphthoic acid to the alkyl halide is about 1:1 to about 1:2. A suitable amount of the alkaline compound used in the former method is about 2 to 2.5 times by weight to the amount of the 1,4-dihydroxy-2-naphthoic acid. A suitable temperature for the reaction is preferably about 35° to 60° C. Reaction of the 1,4-dihydroxy-2-naphthoic acid with the substituted alkyl halide in the presence of an alkaline compound is conducted in an inert atmosphere (such as nitrogen gas).

Alternatively, 1,4-dihydroxy-2-naphthoic acid prepared as described above can be reacted with a substituted alcohol in toluene, anisole, xylene and toluene-other solvent mixtures containing 80% by weight or more toluene (such as toluene-dioxane (4:1 by wt.)) in the presence of an acid catalyst. The sulfonamido alcohol derivatives produced as described above can be used as the starting material substituted alcohols in the latter method. A suitable molar ratio of the 1,4-dihydroxy-2-naphthoic acid to the substituted alcohol is about 1:2. Suitable acid catalysts which can be used include, e.g., sulfuric acid, p-toluenesulfonic acid, methanesulfonic acid.

The product obtained, a 1-hydroxy-4-(substituted alkoxy)-2-naphthoic acid derivative, is then converted into the acid chloride thereof or into the phenyl ester thereof using conventional methods, which is then subjected to a condensation with an amine, such as, for example, aniline, 2,4-di-tert-amylphenoxypropylamine, etc., to prepare the final product, the coupler. Conversion to the acid chloride can be using the procedures as set forth in *Org. Synth. Coll.*, Vol. 1, 12 (1932) and *Helv.* 42, 1653 (1959). Preparation of the phenyl ester can be according to the description set forth in *Org. Synth. Coll.*, Vol. 4, 390, 178 (1963) and Chem. Ind., 2102 (1964). Examples of reactants which can be used to obtain the phenyl ester include phenols, such as phenol, m-cresol and p-nitrophenol. A suitable molar ratio of the acid chloride to the amine in the condensation is about 1:3. Suitable amines which can be used include 2,4-di-tert-amylphenoxybutylamine, n-dodecyloxypropylamine, N-cyano-N-hexadecylamine, o-tetradecyloxyaniline, etc. A suitable reaction temperature is about 80° C. with a reaction time of about 3 to 5 hours in a solvent, such as acetonitrile, tetrahydrofuran, etc.

In case of a phenol type coupler, after the hydroxyl group at the 1-position of the 1,4-dihydroxybenzene derivative has been protected by etherification with, for example, pyrayl ether (e.g., as described in M. G. Dauben and H. L. Bradlow, *J. Amer. Chem. Soc.*, 74, 559 (1952)), or after the 1-hydroxy group and the 2-acetylamino group of the 1,4-dihydroxybenzene derivative are mutually reacted to form an oxazole ring using the method described in Japanese Patent Application (OPI) No. 69572/1976, is subjected to an alkoxylation of the 4-hydroxy group with an appropriate substituted alkylhalide catalyzed by an alkali. A suitable molar ratio of the 1,4-dihydroxybenzene derivative to the alkyl halide is about 1:1.5 to about 1:2.0 with a suitable temperature of reaction being about 60° to 85° C. Suitable examples of alkali catalysts which can be used include potassium carbonate, sodium methoxide, sodium ethoxide, sodium hydroxide, etc. A suitable amount of the alkali catalyst used in this step is about 1.5 to 2.0 times by weight to the weight of 1,4-dihydroxybenzene derivative. Suitable example of solvents which can be used in this step include methaol, ethanol, acetone, dimethylformamide (DMF), etc.

Then, the oxazole ring is cleaved with an acid (such as hydrochloric acid, etc.) at a temperature of about 80° C. to obtain a 1-hydroxy-4-(substituted alkoxy)-2-aminobenzene derivative. The amino group at the 2-position of the benzene derivative obtained is reacted with an appropriate acid chloride with a suitable molar ratio of the acid chloride to the benzene derivative being 1:1, if necessary, in the presence of a dehydrohalogenating agent (such as pyridine, quinoline, triethylamine, etc.) to obtain the desired coupler.

Representative examples of the synthesis of couplers of the present invention are described below. Unless otherwise indicated, all parts, percents, ratios and the like are by weight.

SYNTHESIS EXAMPLE 1

1-Hydroxy-4-(β-methanesulfonamidoethoxy)-N-[β-(2,4-di-tert-amylphenoxy)propyl]-2-naphthamide [Coupler (6)]

41 g (0.2 mole) of 1,4-dihydroxynaphthoic acid was dissolved in 200 ml DMF, into which was added dropwise 80 g of a 28% methanol solution of sodium methoxide (0.4 mole) and bubbling nitrogen therethrough at room temperature. Then, while controlling the reaction temperature between 35°–40° C., 25.2 g (0.16 mole) of β-methanesulfonamidoethyl chloride was added and the mixture was stirred for 1 hour. Finally, the solution was poured into a mixture of 100 ml of concentrated (36%) hydrochloric acid and 500 ml of water to separate a crystalline product, which was filtered. The crystalline product was purified by refluxing with methanol and, thus, 20.8 g of 1-hydroxy-4-(β-methanesulfonamidoethoxy)-2-naphthoic acid was obtained with a yield of 40%.

In 150 ml toluene, 9.8 g of the thus-synthesized carboxylic acid (0.03 mole) and 5.8 g (0.045 mole) of p-nitrophenol were stirred while refluxing, to which 7.2 g (0.06 mole) of thionyl chloride was added dropwise with stirring for 3 hours at the same temperature. Then, the temperature was decreased to room temperature whereby a crystalline product precipitated. The product was the p-nitrophenyl ester derivative and 12.9 g (yield=96%) was obtained.

Then, to 11.2 g (0.025 mole) of the thus-prepared 1-hydroxy-4-(β-methanesulfonamidoethoxy)-2-(4-nitrophenoxycarbonyl)naphthalene in 200 ml of acetonitrile, 9.0 g (0.03 mole) of N-(γ-2,4-di-tert-amylphenoxy)-propylamine was added under stirring while refluxing. After 3 hours, the acetonitrile was removed from the reaction mixture under a reduced pressure, and 13.7 g (yield=92%) of Coupler (6) was obtained by filtration. M.P. of Coupler (6): 141°–142° C.

SYNTHESIS EXAMPLE 2

1-Hydroxy-4-(γ-morpholinosulfonylpropyloxy)-N-[γ-(2,4-di-tert-amylphenoxy)propyl]-2-naphthamide [Coupler (10)]

41 g (0.2 mole) of 1,4-dihydroxynaphthoic acid was dissolved in 200 ml of DMF, to which, under a nitrogen gas atmosphere, was added dropwise 80 g of a 28% methanol solution of sodium methoxide (0.4 mole) at room temperature. Then, while controlling the reaction temperature between 35° and 40° C., 44 g (0.2 mole) of γ-morpholinosulfonylpropyl chloride was added with stirring for 1 hour. Finally, the solution was poured into a mixture of 100 ml of conc. (36%) HCl and 500 ml of water to separate out 1-hydroxy-4-(γ-morpholinosulfonylpropyloxy)-2-naphthoic acid in a crystalline form. Coupler (10) was synthesized by further repeating procedures similar to those set forth in Example 1 described above. M.P. of Coupler (10): 161°–163° C.

SYNTHESIS EXAMPLE 3

4-(β-Methanesulfonamidoethoxy)-5-methyl-2-[α-(2,4-di-tert-amylphenoxy)butyramido]phenol [Coupler (4)]

5.18 g of 2-acetylamino-4-methanesulfonyloxy-5-methylphenol and 0.8 g of p-toluenesulfonic acid were added to 100 ml of toluene and heated at reflux for 12 hours. After cooling and washing with water, concentration under a reduced pressure yielded crude crystals of 5-methanesulfonyloxy-2,6-dimethylbenzoxazole. Immediately the product was dissolved in 50 ml of methanol, to which 5 ml of water containing 2 g of sodium hydroxide was added. A crystalline product was obtained after 1 hour of reflux followed by neutralization with hydrochloric acid after cooling.

Recrystallization from acetonitrile gave 3.0 g of 5-hydroxy-2,6-dimethylbenzoxazole having a melting point 198°–199.5° C.

2.0 g (0.012 mole) of the benzoxazole compound thus-prepared was dissolved in 20 ml of methanol and refluxed for 8 hours after the addition of 4.0 g (0.026 mole) of β-methanesulfonamidoethyl chloride and sodium methoxide.

After cooling and addition of 50 ml of water, the mixture was acidified with glacial acetic acid and was stirred under ice cooling whereby crystals deposited. The crystals were separated by filtration and refluxed for 2 hours together with 8 ml of ethanol and 6 ml of 6 N hydrochloric acid. Upon cooling, the crystals deposited were separated by filtration. Recrystallization from acetonitrile yielded the hydrochloric acid salt of 2-amino-4-(β-methanesulfonamidoethoxy)-5-methylphenol (decomposed at 190° C.).

3.0 g (0.01 mole) of this product was added to 30 ml of acetonitrile, to which 3.5 g (0.01 mole) of α-(2,4-di-tert-amylphenoxybutyryl chloride was added dropwise while stirring and refluxing. After agitation for an additional hour while refluxing, the acetonitrile was removed by distillation under a reduced pressure, and to the remaining oily substance ethanol and n-hexane were added whereby Coupler (4) separated as crystals. M.P. of Coupler (4): 145°–146° C.

One or more of the couplers of this invention can be used to produce a silver halide color photographic material using the coupler of the present invention.

The following types of known couplers may also be incorporated in the photographic material which contains the couplers of the present invention. For example, the cyan dye forming couplers set forth in, for example, U.S. Pat. Nos. 2,474,293, 3,034,892, 3,592,383, 3,311,476, 3,476,563, etc., compounds which can release development inhibiting compounds during color development (referred to DIR couplers or DIR materials) set forth, for example, in U.S. Pat. Nos. 3,632,345, 3,227,554, 3,379,529, etc., the yellow dye forming couplers disclosed, for example, in German Patent Application (OLS) No. 2,213,461, U.S. Pat. No. 3,510,306, etc., and the magenta dye forming couplers disclosed in, for example, U.S. Pat. No. 3,615,506, Japanese Patent Application (OPI) No. 56050/1973, German Patent Application (OLS) No. 2,418,959, etc.

One or more of these couplers can be incorporated in the same layer of the photographic material, or a coupler may be present in two or more layers thereof, depending on the requirements on the characteristics thereof.

Suitable silver halide emulsions which can be used in the present invention include those containing silver chloride and silver bromide as well as mixed halides of silver, such as silver chlorobromide, silver iodobromide, silver chloriodobromide, etc.

The silver halide grains of these emulsions may be of a cubic form, an octahedral form, or may have a mixed crystalline structure.

The silver halide grain size distribution may be narrow or broad, and is not particularly limited. Suitable methods of preparing the silver halide emulsion which can be used include those well known in the art, such as the single and double jet process, the controlled double jet process, etc.

Two or more types of silver halide emulsions which have been prepared separately using different processes can be employed. The grain structure of the silver halide may be uniform or different from the surface to the interior, or may be of the so-called "conversion" type as described in British Pat. No. 635,841 and U.S. Pat. No. 3,622,318.

Further, silver halide grains which provide latent images primarily at the surface thereof or in the interior can be employed in the present invention.

The silver halide emulsions used in this invention may be chemically sensitized using well-known chemical sensitizers including N,N,N'-trimethylthiourea, the complex salts of monovalent gold such as the thiocyanates or the thiosulfates, etc., stannous chloride, hexamethylenetetramine, etc.

The layers of the photographic material can be coated using any known coating method including dip coating, air-knife coating, curtain coating, extrusion coating using a hopper as described in U.S. Pat. No. 2,681,294 and using a simultaneous multilayer coating as set forth in U.S. Pat. Nos. 2,761,791, 3,508,947, 2,941,898, 3,526,528, etc.

Suitable hydrophilic high molecular weight materials which can be present in the photographic coatings of the present invention include gelatin, cellulose derivatives, such as carboxymethylcellulose, hydroxyethylcellulose, etc., carbohydrate derivatives, such as starch derivatives, synthetic hydrophilic colloid materials, such as poly(vinyl alcohol), poly(N-vinylpyrrolidone), copolymers containing acrylic acid, polyacrylamide and the derivatives or partially hydrolyzed products of the above-described polymers, etc. Of these, the most representative is gelatin and gelatin is most generally used. The gelatin can be partly or completely replaced by a synthetic polymer or a gelatin derivative.

The photographic materials of the present invention may comprise photographic emulsions spectrally sensitized or supersensitized so as to be sensitive to blue, green or red light using cyanine dyes, such as cyanine, merocyanine, carbocyanine, etc., dyes, alone or as combinations thereof or in combination with styryl dyes. Descriptions of suitable spectral sensitization techniques appear in, for example, U.S. Pat. No. 2,493,748 for the blue region, U.S. Pat. No. 2,688,545 for the green region and U.S. Pat. No. 3,511,664 for the red region.

The photographic emulsions used in the present invention may contain a stabilizer or an anti-foggant well-known in the art (e.g., 4-hydroxy-6-methyl-1,3,3a,7-tetrazaindene, 3-methylbenzothiazole, 1-phenyl-5-mercaptotetrazole, mercury compounds, mercapto compounds, certain metal salts, etc.).

A synthetic polymeric material can be mixed with the hydrophilic colloid such as gelatin in the photographic emulsion layer and other layers of the photographic color material of the present invention. A typical example of such a polymeric material is an aqueous latex of vinyl polymers as disclosed in U.S. Pat. No. 2,376,005, etc.

Various processes for dye image formation based on a number of different types of photographic materials can be used in the present invention. First, the coupler-in-developer type color process is suitable in which the silver halide photographic material is processed with a color developing solution which contains an aromatic primary amine color developing agent and a coupler whereby a water-insoluble or non-diffusible dye image results within the emulsion layer. Couplers (1), (11) and (16) illustrated hereinbefore can be used for such a process. Another process which can be used comprises processing a photographic material containing a non-diffusible coupler in a silver halide emulsion layer with an alkaline developing solution containing an aromatic primary amine color developing agent to obtain a water-insoluble or non-diffusible dye image in the emulsion layer. Couplers (2), (7), (9) and (23) described hereinbefore can be used for this type of process.

Couplers of the present invention comprising phenol or $\alpha$-naphthol derivatives are usually dispersed into the photographic emulsion in the form of a solution using aqueous or organic solvent systems.

Of the couplers of the present invention, oil-soluble, non-diffusible couplers which are used for the coupler incorporated color process are generally incorporated into the photographic emulsion in the form of minute colloidal particles thereof after the couplers is dissolved in a suitable organic solvent.

Methods for coupler dispersion suitable for use in the present invention are described in U.S. Pat. No. 3,676,131. Organic solvents, which are used to dissolve the coupler, which are insoluble or only sparingly soluble in water and having high boiling points remain in the photographic color material along with the coupler. Examples of these solvents include substituted hydrocarbons, carboxylic acid esters, carboxylic acid amides, phosphoric acid esters and ethers. Specific examples of such couplers include di-n-butyl phthalate, diisooctyl acetate, di-n-butyl sebacate, tricresyl phosphate, tri-n-hexyl phosphate, tri-cyclo-hexyl phosphate, N,N-diethylcaprylamide, butyl-n-pentadecyl phenyl ether, chlorinated paraffin, butyl benzoate, pentyl o-methylbenzoate, propyl 2,4-dichlorobenzoate, etc. In addition to these low-volatile solvents, an auxiliary solvent which promotes coupler dissolution and which can be removed during the production of the photographic material can be advantageously used. Examples of suitable volatile solvents include propylene carbonate, ethyl acetate, butyl acetate, cyclohexanol, tetrahydrofuran, cyclohexanone, etc.

Surface active agents are advantageously used in order to disperse the oil-soluble internal coupler in the form of extremely fine particles into the hydrophilic polymeric matrix of the photographic emulsion. Specifically, anionic surfactants, such as sodium cetyl sulfate, sodium p-dodecylbenzenesulfonate, sodium nonylnaphthalene sulfonate, sodium di(2-ethylhexyl)-$\alpha$-sulfosuccinate, etc., and nonionic surface active agents, such as sorbitan sesquioleate, sorbitan mono-laurate, etc., can be used.

The dispersion of the oil-soluble coupler can be achieved using an emulsifying homogenizer, a colloid mill, an ultrasonic emulsifier, etc.

Examples of silver halide light-sensitive materials in which the coupler of the present invention can be used include color negative films, color positive films, color reversal films, color papers and other color photographic products for general use. Further, the couplers of the present invention can be used in color direct positive products, monochromatic products, color radiographic products, etc.

The couplers of the present invention can be used in multilayer color photographic materials of the conventional type (e.g., those described in U.S. Pat. Nos. 3,726,681, 3,516,831, British Pat. No. 923,045, etc.), in the processes set forth in Japanese Patent Application (OPI) No. 5179/1975, and also in the methods disclosed in German Patent Application (OLS) No. 2,322,165 and U.S. Pat. No. 3,703,375 in which they are used in combination with a DIR compound.

A preferred amount of the coupler of this invention when incorporated into a photographic material, which can be varied depending on the requirements, ranges between about 10 and about 1,500 g, most preferably 10 to 300 g, per mole of silver halide.

Silver halide photographic materials of the present invention comprise a support and various coatings thereon, such as a silver halide emulsion layer, an intermediate layer, an antihalation layer, a protective layer, a yellow filter layer, a backing layer, a mordanting polymer layer, a layer for preventing stains by the developer, etc. The silver halide emulsion layers for color photography comprise a red sensitive silver halide emulsion layer, a green sensitive silver halide emulsion layer and a blue sensitive silver halide emulsion layer. There is no particular limitation on the layer arrangement thereof, and further each of these layers may be divided into two or more layers.

When a p-substituted phenol derivative is present in the silver halide emulsion layer or in an adjacent layer thereto of the photographic material produced in accordance with the present invention, the stability of the finished color image is advantageously enhanced. Particularly effective p-substituted phenol derivatives which can be used include the hydroquinone derivatives disclosed in U.S. Pat. Nos. 2,360,290, 2,418,613, 2,675,314, 2,701,197, 2,704,713, 2,710,801, 2,728,659, 2,732,300, 2,735,765 and 2,816,028, the gallic acid derivatives set forth in U.S. Pat. Nos. 3,457,079 and 3,069,262, Japanese Patent Publication No. 13496/1968, the p-alkoxyphenol derivatives disclosed in U.S. Pat. No. 2,735,765 and Japanese Patent Application (OPI) No. 4738/1972, the p-oxyphenol derivatives described in U.S. Pat. Nos. 3,432,300, 3,573,050, 3,574,627 and 3,764,337.

An ultraviolet absorbing agent may be advantageously employed in order to improve the fastness of the dye images formed. The ultraviolet absorbing agent can be present either in the silver halide emulsion layer itself or in layers adjacent thereto. Those ultraviolet absorbing agents described in, for example, U.S. Pat. Nos. 3,250,617, 3,253,921, etc., can be used.

The silver halide emulsion and other layers can be hardened using any conventionally known methods employing aldehyde compounds, such as formaldehyde, glutaraldehyde, etc., ketone compounds, such as diacetyl or cyclopentanedione, compounds having a reactive halogen, such as bis(2-chloroethylurea), 2-hydroxy-4,6-dichloro-1,3,5-triazine, and those described in U.S. Pat. Nos. 3,288,775, 2,732,303, 3,125,449 and 1,167,207, compounds having a reactive olefinic group, such as divinyl sulfone, 5-acetyl-1,3-diacryloylhexahydro-1,3,5-triazine, and those set forth in U.S. Pat. Nos. 3,635,718 and 3,232,763, British Pat. No. 994,869, etc., N-methylol compounds, such as N-hydroxymethyl phthalimide and those set forth in U.S. Pat. Nos. 2,732,316 and 2,586,168, etc., isocyanate compounds disclosed in U.S. Pat. No. 3,103,437, aziridine compounds set forth in U.S. Pat. Nos. 3,017,280 and 2,983,611, etc., acid derivatives described in U.S. Pat. Nos. 2,725,294 and 2,725,295, etc., carbodiimide derivatives, such as those described in U.S. Pat. No. 3,100,702, etc., epoxy compounds set forth in, for example, U.S. Pat. No. 3,091,537, isoxazoles disclosed in U.S. Pat. Nos. 3,321,313 and 3,543,292, halocarboxyaldehyde compounds including mucochloric acid, dioxane derivatives, such as dihydroxydioxane, dichlorodioxane, etc., or inorganic hardening agents such as chrome alum, zirconium sulfate, etc.

Precursors of hardening agents can also be used with examples of such precursors including alkali metal bisulfite/aldehyde adducts, the methylol derivative of hydantoin, primary aliphatic nitro alcohols, etc.

The color photographic material of the present invention can be subjected to conventional and well known processings comprising, after exposure, color development, bleaching and fixing. Each processing step may be combined with another using a processing agent capable of accomplishing the corresponding functions. A typical example of such a combined processing is a mono-bath process using a blix solution.

Depending on the requirements, the development processing can include additional steps such as prehardening, neutralization, primary development (black-and-white development), image stabilization, washing with water, etc. The processing temperature, which is determined depending on the kind of photographic material as well as by the processing composition, is sometimes below about 18° C. but, in most cases, is not lower than 18° C.

A particularly useful temperature range is from about 20° to 60° C. The temperature may be varied from one processing step to another in the processing.

A color developer comprises an aqueous alkaline solution with a pH not lower than about 8, and more preferably between 9 and 12, containing a color developing agent the oxidation product of which is capable of reacting with a coupler to form a dye.

Suitable color developing agents which can be used include, for example, 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 4-amino-3-methyl-N-ethyl-N-$\beta$-methanesulfamidoethylaniline, 4-amino-N,N-dimethylaniline, 4-amino-3-methoxy-N,N-diethylaniline, 4-amino-3-methyl-N-ethyl-N-$\beta$-methoxyethylaniline, 4-amino-3-methoxy-N-ethyl-N-$\beta$-methoxyethylaniline, 4-amino-3-$\beta$-methanesulfamidoethyl-N,N-diethylaniline, and the salts thereof, such as the sulfates, the hydrochlorides, the sulfites, the p-toluenesulfonates, etc. Other color developing agents which can be used as described in U.S. Pat. Nos. 2,592,364 and 2,193,015, Japanese Patent Application (OPI) No. 64933/1973, L.F.A. Mason, *Photographic Processing Chemistry*, pp. 226–229, Focal Press, London (1966), etc.

Each of the above-described compounds can be used in conjunction with 3-pyrazolidone derivatives. Further, a number of additives well-known in the art may be present in the color developer.

The coupler of this invention can also be incorporated into the color developer and a suitable amount of the coupler of this invention which can be used in the color developing solution is about 0.5 to 20 g per liter of the developing solution.

The photographic material of the present invention is subjected to bleaching after color development. This step may be combined with fixing, whereby the processing solution contains a fixing agent in addition to a bleaching agent.

Suitable bleaching agents include ferricyanide salts, bichromate salts, water-soluble cobalt(III) salts, water-soluble copper(II) salts, water-soluble quinones, nitrosophenol, polyvalent metal compounds containing Fe(III), Co(III), Cu(II), with complex salts of such metals with organic acids, such as, for example, ethylenediamine tetraacetic acid, nitrilotriacetic acid, imidoacetic acid, N-hydroxyethylethylenediamine triacetic acid and other amino-polycarboxylic acid, malonic acid, tartaric acid, malic acid, diglycolic acid, dithioglycolic acid and 2,6-dipicolic acid copper complex salt, etc., being particularly preferred, peracids, such as alkyl peracids, persulfates, permanganates, hydrogen peroxide, etc., hypochlorites, etc.

Other additives, such as bleach accelerating agents as disclosed in U.S. Pat. Nos. 3,042,520 and 3,241,966, Japanese Patent Publication Nos. 8506/1970 and 8836/1970, etc., can be further added to the bleaching solution.

It has been found that the couplers in accordance with the present invention can be used even for silver halide photographic materials of the low silver content type in which the amount of silver halide in the emulsion is from several to one hundred times smaller than that of the ordinary type. Using such a photosensitive material, color images of sufficiently high density can be obtained using the color intensification process in which a peroxide or a cobalt complex salt is employed (for example, as disclosed in German Patent Application (OLS) No. 2,357,694, U.S. Pat. Nos. 3,674,490 and 3,761,265, German Patent Application (OLS) Nos. 2,044,833, 2,056,359, 2,056,360 and 2,226,770, Japanese Patent Application (OPI) Nos. 9728/1973 and 9729/1973, etc.).

The present invention is further described more specifically by reference to the following examples thereof.

EXAMPLE 1

10 g of Coupler (2), 2-chloro-4-($\beta$-methanesulfonamidoethoxy)-3-methyl-6-[$\alpha$-(2,4-di-tert-amylphenoxy)butyramido]phenol, was heated to 50° C. together with 10 ml of di-n-butyl phthalate and 20 ml of ethyl acetate to yield a homogeneous solution. The resulting solution was added to 100 ml of an aqueous solution containing 10 g of gelatin and 0.5 g of sodium p-dodecylbenzenesulfonate, and the total volume was agitated vigorously using a high-speed agitator for 20 minutes whereby the coupler was dispersed in minute droplets together with the solvent.

69.4 g of this dispersion was added to 100 g of a photographic emulsion comprising 0.03 mol of silver chloro-iodide (bromide content=50 mol%) and 8 g of gelatin.

After the addition of 12 ml of a 2% aqueous solution of the sodium salt of 2-hydroxy-4,6-dichloro-s-triazine as a hardener and adjustment to a pH of 6.5, the emulsion was coated on a cellulose triacetate film in a silver coating rate of $7.5 \times 10^{-3}$ mol/m². The photographic material thus-prepared was designated Sample A. The content of the coupler was $1.87 \times 10^{-3}$ mol/m² in Sample A.

The same processes were repeated to prepare a Comparative Sample B except that in place of Coupler (2), 10 g of 4,6-dichloro-5-methyl-2- [$\alpha$-(2',4'-di-tert-amylphenoxy)butyramido]phenol (Coupler (a)) was employed and 55.7 g of the emulsified dispersion was added.

Sample B had a substantially equal coupler content to that for Sample A, i.e., $1.89 \times 10^{-3}$ mol/m².

After sensitometric exposure to a step wedge, each sample was subjected to the following processings in the order listed.

| 1. | Color Development | 24° C. | 8 minutes |
|---|---|---|---|
| 2. | Washing with Water | " | 1 minute |
| 3. | First Fixing | " | 4 minutes |
| 4. | Washing with Water | " | 3 minutes |
| 5. | Bleaching | " | 6 minutes |
| 6. | Washing with Water | " | 3 minutes |
| 7. | Second Fixing | " | 4 minutes |
| 8. | Washing with Water | " | 10 minutes |

The processing solutions used had the following compositions.

| Color Developer | |
|---|---|
| Sodium Sulfite (anhydrous) | 3.0 g |
| 4-Amino-3-methyl-N,N-diethylaniline (HCl salt) | 2.5 g |
| Sodium Carbonate (monohydrate) | 47.0 g |
| Potassium Bromide | 2.0 g |
| Water to make | 1,000 ml |

| First and Second Fixing Solution | |
|---|---|
| Sodium Thiosulfate | 150 g |
| Sodium Sulfite | 15 g |
| Glacial Acetic Acid (28% aq. soln.) | 48 ml |
| Boric Acid | 7.5 g |
| Water to make | 1,000 ml |

| Bleach Bath | |
|---|---|
| Potassium Bromide | 20 g |
| Potassium Ferricyanide | 100 g |
| Glacial Acetic Acid (28% aq. soln.) | 20 ml |
| Sodium Acetate | 40 g |
| Water to make | 1,000 ml |

The optical density to red light of each sample was measured, and the results obtained are shown in Table 1 below.

TABLE 1

| Sample | Coupler | Coupler Coating Rate (mol/m²) | $D_{fog}$ | Relative* Sensitivity | Gamma | $D_{max}$ |
|---|---|---|---|---|---|---|
| A | (2) | $1.87 \times 10^{-3}$ | 0.05 | 100 | 3.60 | 3.75 |
| B | (a) | $1.89 \times 10^{-3}$ | 0.05 | 94 | 3.10 | 3.15 |

*The relative amount of exposure required to obtain a density of $D_{fog} + 0.10$.

Next, the time of the processing for the color development was changed for Samples A and B to determine the dependence of the maximum density for red light on the development time. The results obtained are given in Table 2 below.

TABLE 2

| | | Developing Time (minutes) | | |
|---|---|---|---|---|
| Sample | Coupler | 4 | 8 | 15 |
| A | (2) | 3.65 | 3.75 | 3.80 |
| B | (a) | 3.00 | 3.15 | 3.35 |

The results obtained above clearly demonstrate that the coupler of the present invention in which the active site is substituted with a $\beta$-methanesulfonamidoethoxy group results in a higher sensitivity, a better gradation and a higher color density in comparison with a coupler such as Coupler (a) in which the active site is substituted with a chlorine atom, and that such a large density can be developed in a short processing time, enabling a reduction in the processing period of time.

When Coupler (3) was used in place of Coupler (2) with the same processing, similarly advantageous results were obtained for $D_{max}$, gradation and photographic speed, showing the superiority of the coupler of this invention to a coupler in which the active site is substituted with a chlorine atom.

EXAMPLE 2

To 10 g of Coupler (6), i.e., 1-hydroxy-4-($\beta$-methanesulfonamidoethoxy)-N-[$\gamma$-(2,4-di-tert-amyl-phenoxy)-propyl]-2-naphthamide were added 10 ml of tricresyl phosphate, 20 ml of ethyl acetate and 0.5 g of sodium di(2-ethylhexyl)-$\alpha$-sulfosuccinate. The mixture was warmed to 50° C. to promote the dissolution, then the mixture was added to 100 ml of an aqueous solution containing 10 g of gelatin. Emulsification was carried out using a homogenizer. The resultant product was designated Dispersion (A).

To 100 g of a silver iodobromide emulsion (iodide content=7 mol%; silver content=$3.5 \times 10^{-2}$ mol; content of gelatin=6 g) were added 43.1 g of Dispersion (A), then 5 ml of a 2% methanol solution of 5-methyl-7-hydroxy-1,3,4,7a-tetrazaindene and 6.5 ml of a 2% aqueous solution of sodium 2-hydroxy-4,6-dichloro-s-triazine as hardening agent. Finally, after the adjustment of the pH to 6.5, the mixture was coated on a cellulose triacetate film in a coupler coating rate of $2.03 \times 10^{-3}$ mol/m². This film was designated Sample C.

For the purposes of comparison, Coupler (b) which had the same nuclear structure as Coupler (6) but with the active site unsubstituted was used to prepare Dispersion (B) using the same procedures employed for Dispersion (A).

To 200 g of the emulsion described above was added 32.4 g of Dispersion (B) and the resulting emulsion was coated on a cellulose triacetate film to produce Sample D.

Similarly, Samples E, F, G, H and J were prepared using a series of closely related couplers and according to the conditions summarized in the table below.

| Sample | Coupler | | Dispersion | Weight Ratio of Dispersion to Emulsion | Coupler Coating Rate (mol/m²) |
|---|---|---|---|---|---|
| C | (6) | | A | 43.1:100 | $2.03 \times 10^{-3}$ |
| D | (b) | similar to (6) with the active site unsubstituted | B | 32.4:200 | $2.08 \times 10^{-3}$ |
| E | (c) | similar to (6) with the active site substituted with a chlorine atom | C | 34.7:100 | $2.05 \times 10^{-3}$ |
| F | (d) | similar to (6) with the active site substituted with an ethoxy group | D | 35.0:100 | $2.06 \times 10^{-3}$ |
| G | (e) | similar to (6) with the active site substituted with a butylcarbamyl-methoxy group | E | 41.3:100 | $2.07 \times 10^{-3}$ |
| H | (f) | similar to (6) with the active site substituted with an ethoxycarbonyl-methoxy group | F | 39.4:100 | $2.05 \times 10^{-3}$ |
| J | (j) | 1-Hydroxy-N-[$\gamma$-(2-ethylhexyloxy)-propyl]-2-naphthamide | J | 25.0:200 | $2.06 \times 10^{-3}$ |

Each sample contained appropriate amounts of stabilizer as well as hardening agent corresponding to the amount of silver and gelatin.

After sensitometric step wedge exposure, each of these seven samples was subjected to the following processings.

| 1. | Color Development | 38° C. | 3 minutes |
|---|---|---|---|
| 2. | Stop Bath | " | 1 minute |
| 3. | Washing with Water | " | 1 minute |
| 4. | Bleaching | " | 2 minutes |
| 5. | Washing with Water | " | 1 minute |
| 6. | Fixing | " | 2 minutes |
| 7. | Washing with Water | " | 1 minute |
| 8. | Stabilizing Bath | " | 1 minute |

The processing solutions used had the following compositions.

| Color Developer | |
|---|---|
| Sodium Hydroxide | 2 g |
| Sodium Sulfite | 2 g |
| Potassium Bromide | 0.4 g |
| Sodium Chloride | 1 g |
| Borax | 4 g |
| Hydroxylamine Sulfate | 2 g |
| Disodium Ethylenediamine Tetraacetate (dihydrate) | 2 g |
| 4-Amino-3-methyl-N-ethyl-N-($\beta$-hydroxyethyl)aniline Monosulfate | 4 g |
| Water to make | 1,000 ml |

| Stopping Bath | |
|---|---|
| Sodium Thiosulfate | 10 g |
| Ammonium Thiosulfate (70% aq. soln.) | 30 ml |
| Acetic Acid | 30 ml |
| Sodium Acetate | 5 g |
| Potassium Alum | 15 g |
| Water to make | 1,000 ml |

| Bleach | |
|---|---|
| Fe(III) . 2Na Ethylenediamine Tetraacetate (dihydrate) | 100 g |
| Potassium Bromide | 50 g |
| Ammonium Nitrate | 50 g |
| Boric Acid | 5 g |
| Aqueous Ammonia | to adjust pH to 5.0 |
| Water to make | 1,000 ml |

| Fixing Solution | |
|---|---|
| Sodium Thiosulfate | 150 g |
| Sodium Sulfite | 15 g |
| Borax | 12 g |
| Glacial Acetic Acid | 15 ml |
| Potassium Alum | 20 g |

-continued

| Fixing Solution | |
|---|---|
| Water to make | 1,000 ml |

| Stabilizing Bath | |
|---|---|
| Boric Acid | 5 g |
| Sodium Citrate | 5 g |
| Sodium Metaborate (tetrahydrate) | 3 g |
| Potassium Alum | 15 g |
| Water to make | 1,000 ml |

After processing, the optical density to red light of each of these samples, i.e., C, D, E, F, G, H and J, was measured and the results obtained are shown in Table 3 below.

TABLE 3

| Sample | Coupler | Coupler Coating Rate (mol/m²) | $D_{fog}$ | Relative* Sensitivity | Gamma | $D_{max}$ |
|---|---|---|---|---|---|---|
| C | (6) | $2.03 \times 10^{-3}$ | 0.07 | 100 | 2.50 | 3.15 |
| D | (b) | $2.08 \times 10^{-3}$ | 0.07 | 70 | 1.51 | 2.15 |
| E | (c) | $2.05 \times 10^{-3}$ | 0.06 | 73 | 1.68 | 2.30 |
| F | (d) | $2.06 \times 10^{-3}$ | 0.07 | 80 | 1.90 | 1.95 |
| G | (e) | $2.07 \times 10^{-3}$ | 0.06 | 72 | 1.85 | 2.35 |
| H | (f) | $2.05 \times 10^{-3}$ | 0.07 | 85 | 2.05 | 2.52 |
| J | (j) | $2.06 \times 10^{-3}$ | 0.06 | 90 | 2.30 | 1.90 |

*The relative amount of exposure to obtain a density of 0.10 above $D_{fog}$.

These results demonstrate that the coupler of the present invention, coupler (6), containing the β-methanesulfonamidoethoxy group as the substituent at the active site can impart a higher photographic speed, a better tone rendition and a higher $D_{max}$ to the photographic material containing the same in comparison to the corresponding couplers, (b) with an unsubstituted active site, a chlorine substituted active site (c), an ethoxy substituted active site (d), a butylcarbamylmethoxy substituted active site (e), and even Coupler (j) which has a very high rate of coupling as well as a high photographic speed, gamma and $D_{max}$. In addition, no deterioration in granularity of the resulting dye image, which tends to result from strengthened coupling activity, was observed on examination under a microscope.

Similarly desirble results of photographic speed, gamma and $D_{max}$ were obtained when Coupler (8) was used in place of Coupler (6).

EXAMPLE 3

50.0 g of Coupler (3), i.e., 2-chloro-3-methyl-4-(γ-morpholinosulfonylpropyloxy)-6-[α-(2,4-di-tert-amylphenoxy)butyramido]phenol was mixed with 40 ml of di-n-butyl phthalate, 80 ml of ethyl acetate, and 2.0 g of sodium di(2-ethylhexyl)-α-sulfosuccinate. A homogeneous solution was obtained by heating the above mixture to 50° C. and the mixture was added to 400 ml of an aqueous solution containing 40 g of galatin. On agitation, a turbid mixture resulted, which was further emulsified using a homogenizer.

A photographic emulsion was prepared by adding to 1.0 kg of a silver chlorobromide emulsion containing 0.3 mol silver and 70 g of gelatin (bromide content=50 mol%), 200 ml of a 0.01% methanol solution of a red sensitive spectral sensitizer designated Compound I-6 in Japanese Patent Publication No. 22189/1970 corresponding to U.S. Pat. No. 3,635,721, and then 50 ml of a 1% methanol solution of 5-methyl-7-hydroxy-1,3,4,7a-tetrazaindene.

The entire weight of the emulsified dispersion described above was added to all of this emulsion and, further, 30 ml of a 3% acetone solution of triethylenephosphamide was added as hardening agent. Finally, the pH was adjusted to 6.5.

On a substrate comprising baryta paper, both surfaces of which had been treated with polyethylene, a first layer comprising a blue sensitive silver halide emulsion containing Coupler (g), i.e., α-(5,5-dimethyl-2,4-dioxo-oxazolidin-3-yl)-α-pivaloyl-2-chloro-5-[α-(2′,4′-di-tert-amylphenoxy)butylamido]acetanilide was coated in a thickness of 4.0 microns. Then, a gelatin solution was coated thereon in a dry thickness of 1.0 micron, and a third layer comprising a green sensitive silver halide emulsion containing Coupler (h), i.e., 1-(2,4,6-trichlorophenyl)-3-[(2-chloro-5-n-tetradecanamido)anilino]-5-pyrazolone was overcoated in a dry thickness of 2.5 microns. A fourth layer was provided by coating a gelatin solution containing 2-(2′-benzotriazolyl)-4,6-dibutylphenol as a UV absorber in a dry thickness of 2.5 microns.

The red sensitive silver halide emulsion described above was then coated in a thickness of 3.5 microns on dry basis as a fifth layer. As the outermost layer, a gelatin solution was coated in a dry thickness of 0.5 micron.

The color print paper thus-prepared was exposed to a color negative original followed by the processing as described below.

| 1. | Color Development | 30° C. | 6 minutes |
|---|---|---|---|
| 2. | Stop Bath | " | 2 minutes |
| 3. | Washing with Water | " | 2 minutes |
| 4. | Bleach-Fixing | " | 2 minutes |
| 5. | Washing with Water | " | 2 minutes |
| 6. | Stabilizing Bath | " | 2 minutes |

The processing solutions used had the following compositions.

| Color Developing Solution | |
|---|---|
| Benzyl Alcohol | 12 ml |
| Diethylene Glycol | 3.5 ml |
| Sodium Hydroxide | 2.0 g |
| Sodium Sulfite | 2.0 g |
| Potassium Bromide | 0.4 g |
| Sodium Chloride | 1.0 g |
| Borax | 4.0 g |
| Hydroxamine Sulfate | 2.0 g |
| Disodium Ethylenediamine Tetraacetate (dihydrate) | 2.0 g |
| 4-Amino-3-methyl-N-ethyl-N-(β-methanesulfonamidoethyl)aniline sesquisulfate (monohydrate) | 5.0 ml |
| Water to make | 1,000 ml |

| Stop Bath | |
|---|---|
| Sodium Thiosulfate | 10 g |
| Ammonium Thiosulfate (70% aq. soln.) | 30 ml |
| Sodium Acetate | 5 g |
| Acetic Aicd | 30 ml |
| Potassium Alum | 15 g |
| Water to make | 1,000 ml |

| Blix Bath | |
| --- | --- |
| Ferric Sulfate | 20 g |
| Disodium Ethylenediamine Tetraacetate (dihydrate) | 36 g |
| Sodium Carbonate (monohydrate) | 17 g |
| Sodium Sulfite | 5 g |
| Ammonium Thiosulfate (70% aq. soln.) | 100 ml |
| Boric Acid | 5 g |
| pH adjusted to | 6.8 |
| Water to make | 1,000 ml |

| Stabilizing Bath | |
| --- | --- |
| Boric Acid | 5 g |
| Sodium Citrate | 5 g |
| Sodium Metaborate (tetrahydrate) | 3 g |
| Potassium Alum | 15 g |
| Water to make | 1,000 ml |

The resulting color print had an excellent appearance with brilliant colors, exhibiting a superior color reproduction capability. The cyan dye image had an absorption maximum at 673 mμ.

The light fastness of the image was examined by irradiating the print with white fluorescent light at an intensity of 30,000 lux for 20 days. The density change of the cyan dye was 0.03 at the area with an initial reflection density of 1.0. Further, the stability of the image under unfavorable storage conditions was confirmed to be acceptable since storage under a high temperature and high humidity condition of 60° C. and 75% RH for 10 days decreased the cyan density only by 0.06 from the initial value of 1.0.

When a piece of the coated unexposed sample was left at 80% RH for 3 days and another piece at 25° C. and 60% RH for the same period, and then both pieces were subjected to sensitometric step wedge exposure, followed by the processing described above, no significant differences in $D_{max}$, $D_{fog}$ and gamma were observed between the two samples, confirming that the photographic materials of the present invention possess satisfactory stability.

EXAMPLE 4

10 g of Coupler (12), i.e., N-n-hexadecyl-N-cyanoethyl-1-hydroxy-4-(3,5-dimethyl-1,2,4-triazolylsulfonyl-propyloxy)-2-naphthamide, was dissolved in 10 ml of tris-n-hexyl phosphate and 20 ml of ethyl acetate by heating to 50° C. The resulting solution was colloidally dispersed into 100 ml of an aqueous solution containing 0.5 g of sodium p-dodecylbenzenesulfonate and 10 g of gelatin with vigorous stirring.

To 186 g of a reversal type silver iodobromide emulsion (iodide content=3 mol%; Ag content=$8.37 \times 10^{-2}$; gelatin content=13.0 g), were added all of the dispersion thus-prepared and then 12 ml of a 4% aqueous solution of sodium 2-hydroxy-4,6-dichloro-s-triazone. After adjustment of the pH to 7.0, the mixture was coated on a poly(ethylene terephthalate) film in an Ag coating rate of 0.90 g/m².

After sensitometric exposure to optical step wedge, the following processings were carried out.

| 1. | First Development | 30° C. | 3 minutes |
| --- | --- | --- | --- |
| 2. | Washing with Water | " | 0.5 minute |
| 3. | Exposure for Image Reversal | | intensity of 8,000 lux, 1 second |
| 4. | Second Development | 30°C. | 4 minutes |
| 5. | Washing with Water | " | 1 minute |
| 6. | Bleaching | " | 1 minute |
| 7. | Washing with Water | " | 0.5 minute |
| 8. | Fixing | " | 1 minute |
| 9. | Washing with Water | " | 1 minute |

The processing solutions used had the following compositions.

| First Developer | |
| --- | --- |
| 4-(N-Methylamino)phenol Sulfate | 2 g |
| Sodium Sulfite | 90 g |
| Hydroquinone | 8 g |
| Sodium Carbonate (monohydrate) | 52.5 g |
| Potassium Bromide | 5 g |
| Potassium Thiocyanate | 1 g |
| Water to make | 1,000 ml |

| Second Developer | |
| --- | --- |
| Benzyl Alcohol | 5 ml |
| Sodium Sulfite | 5 g |
| Hydroxylamine Hydrochloride | 2 g |
| 4-Amino-3-methyl-N-ethyl-N-(β-ethoxyethyl)aniline p-Toluenesulfonate | 3 g |
| Potassium Bromide | 1 g |
| Sodium Phosphate | 30 g |
| Sodium Hydroxide | 0.5 g |
| Ethylenediamine (70% aq. soln.) | 7 ml |
| Water to make | 1,000 ml |

| Bleaching Bath | |
| --- | --- |
| Potassium Ferricyanide | 100 g |
| Sodium Acetate | 40 g |
| Sodium Sulfite | 20 g |
| Potassium Alum | 30 g |
| Water to make | 1,000 ml |

| Fixing Solution | |
| --- | --- |
| Sodium Thiosulfate | 150 g |
| Sodium Acetate | 70 g |
| Sodium Sulfite | 10 g |
| Potassium Alum | 20 g |
| Water to make | 1,000 ml |

The reversal color image thus-produced had an absorption maximum at 687 mμ exhibiting a superior color hue.

When another piece of the same sample was sensitometrically exposed to an optical step wedge after storage for 3 days at 40° C., 75% RH, followed by the same processing as described above, an equivalent photographic performance as to $D_{max}$, $D_{fog}$, photographic speed, etc., was obtained, confirming that the coupler used was satisfactorily stable.

EXAMPLE 5

A silver iodobromide emulsion containing 4 mol% iodide was coated on a cellulose triacetate film base at a silver coating rate of 120 μg/cm² and in a thickness of 4.0 microns. This film was sensitometrically exposed to a step wedge, and processed with the following color developer at 27° C., for 4 minutes, followed by washing, bleaching, washing, fixing and washing in a manner similar to Example 1. A cyan dye image was obtained.

| Color Developer | |
|---|---|
| Sodium Sulfite | 5 g |
| 4-Amino-3-methyl-N,N-diethylaniline Hydrochloride | 0.6 g |
| Sodium Carbonate (monohydrate) | 15 g |
| Potassium Bromide | 0.5 g |
| Potassium Iodide (0.1% aq. soln.) | 5 ml |
| 2-Acetamido-6-chloro-4-($\beta$-methane-sulfonamidoethoxy)-5-methylphenol (Coupler (1)) | 1.3 g |
| Methanol | 20 ml |
| Sodium Hydroxide | 2 g |
| Water to make | 1,000 ml |

The resultant dye image had a bright cyan appearance with an absorption maximum at 672 m$\mu$.

EXAMPLE 6

10 g of Coupler (5), i.e., 2-chloro-4-($\beta$-N-methyl-methanesulfonamidoethoxy)-3-methyl-6-[$\alpha$-(2,4-di-tert-amylphenoxy)butyramido]phenol was added to and dissolved in 10 ml of di-n-butyl phthalate diluted with 20 ml of ethyl acetate at 50° C. This solution was added to 100 ml of an aqueous solution containing 10 g of gelatin and 0.5 g of sodium p-dodecylbenzenesulfonate, and the resulting mixture was subjected to vigorous mechanical agitation using a high speed agitator for 20 minutes whereby the coupler and the solvent were finely dispersed.

70.9 g of the emulsified dispersion obtained was added to 100 g of a photographic emulsion as described in Example 1, containing 0.03 g of silver chloroiodide (bromide content=50 mol%) and 8 g of gelatin. After the addition of 12 ml of a 2% aqueous solution of sodium 2-hydroxy-4,6-dichloro-s-triazine as a hardening agent and adjustment of the pH to 6.5, the mixture was coated on a cellulose triacetate film in a silver coating rate of $7.7 \times 10^{-8}$ mol/cm$^2$. The photographic material thus-prepared was designated Sample I. The coupler content of Sample I was $1.82 \times 10^{-3}$ mol/m$^2$.

Samples A and B in Example 1 were used as a comparative sample. After sensitometric exposure to an optical step wedge, each sample was processed according to the methods described in Example 3, except that 3 minutes of color development time was used and the color developer was replaced by a color developer having the following composition which differed from the color developer used in Example 3 by the elimination of benzyl alcohol and diethylene glycol.

| Color Developer | |
|---|---|
| Sodium Hydroxide | 2.0 g |
| Sodium Sulfite | 2.0 g |
| Potassium Bromide | 0.4 g |
| Sodium Chloride | 1.0 g |
| Borax | 4.0 g |
| Hydroxylamine Hydrosulfate | 2.0 g |
| Disodium Ethylenediamine Tetraacetate (dihydrate) | 2.0 g |
| 4-Amino-3-methyl-N-ethyl-N-($\beta$-methanesulfonamidoethyl)aniline Sesquisulfate (monohydrate) | 5.0 g |
| Water to make | 1,000 ml |

The optical densities to red light of processed Samples, I, A and B were measured and the results shown in Table 4 below were obtained.

TABLE 4

| Film Sample | Coupler | Coupler Coating Rate (mol/m$^2$) | $D_{fog}$ | Relative* Sensitivity | Gamma | $D_{max}$ |
|---|---|---|---|---|---|---|
| I | (5) | $1.82 \times 10^{-3}$ | 0.05 | 95 | 2.65 | 2.73 |
| A | (2) | $1.87 \times 10^{-3}$ | 0.05 | 100 | 2.75 | 2.95 |
| B | (a) | $1.89 \times 10^{-3}$ | 0.04 | 87 | 2.15 | 2.40 |

*The amount of exposure required to obtain a density of 0.10 above the fog density.

Next, the dependence of the maximum density of red light on the period of color development was determined for each of Samples I, A and B.

The results shown in Table 5 below were obtained.

TABLE 5

| Film Sample | Coupler | Development Time (minutes) 1.5 | 3 |
|---|---|---|---|
| I | (5) | 2.45 | 2.72 |
| A | (2) | 2.82 | 2.93 |
| B | (a) | 1.79 | 2.36 |

These results demonstrate that the coupler of the present invention in which the active site is substituted with a methanesulfonamidoethoxy group gives a higher photographic speed as well as image density and a better tonal rendition than a chlorine-substituted coupler, like Coupler (a). In addition, since such a high density can be developed in a shorter processing time, a reduction in the processing time becomes possible.

While the invention has been described in detail and with reference to specific embodiments thereof, it will be apparent to one skilled in the art that various changes and modifications can be made therein without departing from the spirit and scope thereof.

What is claimed is:

1. A photographic silver halide light-sensitive emulsion containing a cyan dye-forming colorless photographic coupler residue containing an $\alpha$-naphthol nucleus wherein the coupling position capable of reacting with the oxidized product of an aromatic primary amine development agent is substituted with at least one alkoxy group substituted with a sulfonamido or sulfamoyl group as a coupling off group, said sulfonamido or sulfamoyl group being represented by the following general formula (III) or (IV):

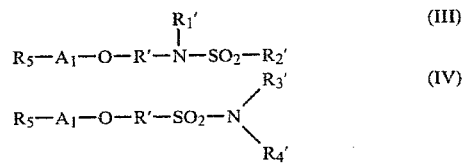

wherein A$_1$ represents said cyan dye-forming coupler residue containing an $\alpha$-naphthol nucleus; R' represents a saturated or unsaturated divalent aliphatic group; wherein R'$_1$ represents a hydrogen atom, an alkyl group containing up to 7 carbon atoms, an alkenyl group containing up to 7 carbon atoms, an aralkyl group with 7 carbon atoms, or an aryl group with 6 to 12 carbon atoms; and R$_2$ represents an alkyl group containing up to 18 carbon atoms, an alkenyl group containing up to 18 carbon atoms, an aralkyl group containing up to 18 carbon atoms, an aryl group containing 6 to 12 carbon atoms or a heterocyclic group selected from the class consisting of a thiazolyl, a benzothiazolyl, an oxazolyl, a pyridyl, a 1,2,4-triazolyl, a pyrazolyl, a benzimidazolyl and a imidazolyl group; $R'_3$ and $R'_4$, which may be the same or different, each represents a hydrogen atom, an alkyl group containing up to 18 carbon atoms, an alkenyl group containing up to 18 carbon atoms, an aralkyl group containing 7 to 18 carbon atoms, an aryl group containing 6 to 12 carbon atoms; and $R_3$ and $R_4$ can combine and form a ring selected from the class consisting of a piperadine, a pyrrolidine, a pyrrole, a morpholine, an imidazole, a benzimidazole, a 1,2,4-triazole, a 1,2,3-triazole and a benzotriazole ring, $R_5$ represents a hydrogen atom, an aliphatic group containing up to 30 carbon atoms, an alkoxy group containing up to 30 carbon atoms, an aryloxy group, an acylamido group, a sulfonamido group, a phosphoramido group, a ureido group, or a carbamyl group, each represented by the general formula (V) to (X):

$$-NH-CO-B \qquad (V)$$

$$-NH-SO_2-B \qquad (VI)$$

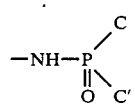  (VII)

$$-NHCONH-B \qquad (VIII)$$

$$-CONH-B \qquad (IX)$$

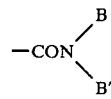  (X)

wherein B and B', which may be the same or different, each represents an aliphatic group containing 1 to 32 carbon atoms, a cycloalkyl group or an aryl group, wherein the alkyl group and the aryl group may be substituted with one or more of a hydrogen atom, a nitro group, a cyano group, a hydroxyl group, a carboxy group, an amino group, an alkyl group, an aryl group, an alkoxycarbonyl group, an acyloxycarbonyl group, an amido group, an imido group, a carbamoyl group, an alkoxy group, or an aryloxyl group; and C and C', which may be the same or different, each represents the groups described for B and additionally an —N—OB group, an —NH—B group, or an —NB$_2$ group.

2. The photographic emulsion of claim 1, wherein the alkyl group, the alkenyl group, and the aryl group represented by $R'_1$, $R'_2$, $R'_3$ and $R'_4$ and the heterocyclic group represented by $R'_2$ may be unsubstituted or substituted with one or more of a halogen atom, a nitro group, a cyano group, a hydroxyl group, a carboxyl group or a sulfo group.

3. The photographic emulsion of claim 1, wherein R contains 1 to 4 carbon atoms.

4. A photographic silver halide light-sensitive material comprising a support having thereon at least one silver halide emulsion layer and containing at least one cyan dye-forming colorless coupler residue containing an α-naphthol nucleus having, at the coupling position, an alkoxy group having at least one sulfonamido or sulfamoyl group as a substituent and represented by one of the following general formula (III) or (IV):

  (III)

  (IV)

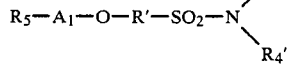

wherein $A_1$ represents said cyan dye-forming coupler residue containing an α-naphthol nucleus; R' represents a saturated or unsaturated divalent aliphatic group; wherein $R'_1$ represents a hydrogen atom, an alkyl group containing up to 7 carbon atoms, an alkenyl group containing up to 7 carbon atoms, an aralkyl group with 7 carbon atoms, or an aryl group with 6 to 12 carbon atoms; and $R_2$ represents an alkyl group containing up to 18 carbon atoms, an alkenyl group containing up to 18 carbon atoms, an aralkyl group containing up to 18 carbon atoms, an aryl group containing 6 to 12 carbon atoms or a heterocyclic group selected from the class consisting of a thiazolyl, a benzothiazolyl, an oxazolyl, a pyridyl, a 1,2,4-triazolyl, a pyrazolyl, a benzimidazolyl and a imidazolyl group; $R'_3$ and $R'_4$, which may be the same or different, each represents a hydrogen atom, an alkyl group containing up to 18 carbon atoms, an alkenyl group containing up to 18 carbon atoms, an aralkyl group containing 7 to 18 carbon atoms, an aryl group containing 6 to 12 carbon atoms; and $R_3$ and $R_4$ can combine and form a ring selected from the class consisting of a piperadine, a pyrrolidine, a pyrrole, a morpholine, an imidazole, a benzimidazole, a 1,2,4-triazole, a 1,2,3-triazole and a benzotriazole ring, $R_5$ represents a hydrogen atom, an aliphatic group containing up to 30 carbon atoms, an alkoxy group containing up to 30 carbon atoms, an aryloxy group, an acylamido group, a sulfonamido group, a phosphoramido group, a ureido group, or a carbamyl group, each represented by the general formula (V) to (X):

$$-NH-CO-B \qquad (V)$$

$$-NH-SO_2-B \qquad (VI)$$

  (VII)

$$-NHCONH-B \qquad (VIII)$$

$$-CONH-B \qquad (IX)$$

  (X)

wherein B and B', which may be the same or different, each represents an aliphatic group containing 1 to 32 carbon atoms, a cycloalkyl group or an aryl group, wherein the alkyl group and the aryl group may be substituted with one or more of a hydrogen atom, a nitro group, a cyano group, a hydroxyl group, a carboxy group, an amino group, an alkyl group, an aryl group, an alkoxycarbonyl group, an acyloxycarbonyl group, an amido group, an imido group, a carbamoyl group, an alkoxy group, or an aryloxyl group; and C and C', which may be the same or different, each represents the groups described for B and additionally an —N—OB group, an —NH—B group, or an —NB$_2$ group.

5. The photographic material of claim 4, wherein the alkyl group, the alkenyl group and the aryl group represented by R'$_1$, R'$_2$, R'$_3$ and R'$_4$ and the heterocyclic group represented by R'$_2$ may be unsubstituted or substituted with one or more of a halogen atom, a nitro group, a cyano group, a hydroxyl group, a carboxyl group or a sulfo group.

6. The photographic material of claim 4, wherein R contains 1 to 4 carbon atoms.

7. A method of forming an image comprising exposing a silver halide light-sensitive photographic material comprising a support having thereon at least one silver halide emulsion layer and developing said exposed silver halide photographic material with a developer containing an aromatic primary amine developing agent in the presence of at least one cyan dye-forming colorless photographic coupler residue containing an α-naphthol nucleus having, at the coupling position, an alkoxy group having at lease at one sulfonamido or sulfamoyl group as a substituent and represented by the following general formula (III) or (IV):

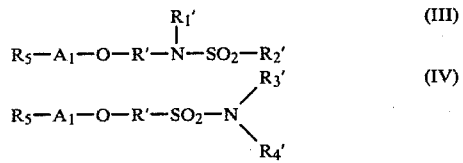

wherein A$_1$ represents said cyan dye-forming coupler residue containing an α-naphthol nucleus; R' represents a saturated or unsaturated divalent aliphatic group; wherein R'$_1$ represents a hydrogen atom, an alkyl group containing up to 7 carbon atoms, an alkenyl group containing up to 7 carbon atoms, an aralkyl group with 7 carbon atoms, or an aryl group with 6 to 12 carbon atoms; and R$_2$ represents an alkyl group containing up to 18 carbon atoms, an alkenyl group containing up to 18 carbon atoms, an aralkyl group containing up to 18 carbon atoms, an aryl group containing 6 to 12 carbon atoms or a heterocyclic group selected from the class consisting of a thiazolyl, a benzothiazolyl, an oxazolyl, a pyridyl, a 1,2,4-triazolyl, a pyrazolyl, a benzimidazolyl and a imidazolyl group; R'$_3$ and R'$_4$, which may be the same or different, each represents a hydrogen atom, an alkyl group containing up to 18 carbon atoms, an alkenyl group containing up to 18 carbon atoms, an aralkyl group containing 7 to 18 carbon atoms, an aryl group containing 6 to 12 carbon atoms; and R$_3$ and R$_4$ can combine and form a ring selected from the class consisting of a piperadine, a pyrrolidine, a pyrrole, a morpholine, an imidazole, a benzimidazole, a 1,2,4-triazole, a 1,2,3-triazole and a benzotriazole ring, R$_5$ represents a hydrogen atom, an aliphatic group containing up to 30 carbon atoms, an alkoxy group containing up to 30 carbon atoms, an aryloxy group, an acylamido group, a sulfonamido group, a phosphoramido group, a ureido group, or a carbamyl group, each represented by the general formula (V) to (X):

wherein B and B', which may be the same or different, each represents an aliphatic group containing 1 to 32 carbon atoms, a cycloalkyl group or an aryl group, wherein the alkyl group and the aryl group may be substituted with one or more of a hydrogen atom, a nitro group, a cyano group, a hydroxyl group, a carboxy group, an amino group, an alkyl group, an aryl group, an alkoxycarbonyl group, an acyloxycarbonyl group, an amido group, an imido group, a carbamoyl group, an alkoxy group, or an aryloxyl group; and C and C', which may be the same or different, each represents the groups described for B and additionally an —N—OB group, an —NH—B group, or an —NB$_2$ group.

8. The method of claim 7, wherein the alkyl group, the alkenyl group and the aryl group represented by R'$_1$, R'$_2$, R'$_3$ and R'$_4$ and the heterocyclic group represented by R'$_2$ may be unsubstituted or substituted with one or more of a halogen atom, a nitro group, a cyano group, a hydroxyl group, a carboxyl group or a sulfo group.

9. The method of claim 7, wherein R contains 1 to 4 carbon atoms.

* * * * *